United States Patent [19]

Lukenbach et al.

[11] Patent Number: 4,696,773

[45] Date of Patent: Sep. 29, 1987

[54] PROCESS FOR THE PREPARATION OF ISETHIONIC ACID

[75] Inventors: Elvin R. Lukenbach, Somerset; Prakash Naik-Satam, East Windsor, both of N.J.; Anthony M. Schwartz, Rockville, Md.

[73] Assignee: Johnson & Johnson Baby Products Company, New Brunswick, N.J.

[21] Appl. No.: 882,660

[22] Filed: Jul. 7, 1986

[51] Int. Cl.$^4$ ........................................... C07C 143/02
[52] U.S. Cl. ................................................. 260/513 R
[58] Field of Search ........................ 260/513 R, 513 B

[56] References Cited

U.S. PATENT DOCUMENTS 4,499,028 2/1985 Longley ............................... 260/513

FOREIGN PATENT DOCUMENTS 0151934 11/1981 Fed. Rep. of Germany ...... 260/513

Primary Examiner—Alan Siegel
Attorney, Agent, or Firm—Steven P. Berman

[57] ABSTRACT

A process for the preparation of isethionic acid involving the reaction of sodium isethionate and hydrogen chloride in an alcoholic solvent is described.

3 Claims, No Drawings

PROCESS FOR THE PREPARATION OF ISETHIONIC ACID

FIELD OF INVENTION

This invention relates to a novel process for the preparation of isethionic acid.

BACKGROUND OF THE INVENTION

This invention relates to a process for the preparation of isethionic acid. Isethionic acid can also be referred to as 2-hydroxyethane sulfonic acid and is of the formula $HOCH_2CH_2SO_3H$. Numerous processes have been suggested in the literature for the preparation of isethionic acid and the related isethionate salts.

A number of these methods are disclosed in C. M. Suter, "The Organic Chemistry of Sulfur", John Wiley & Sons, Inc. New York, 1944 (reprinted 1969), pps. 130–132. An early preparation involved the action of sulfur trioxide upon ethyl alcohol or ether to yield ethionic acid which can then be hydrolyzed to isethionic acid. The sulfonation of barium ethyl sulfate produces similar results. Another preparation involves the action of sulfur trioxide upon ethylene to form crystals of carbyl sulfate that hydrolyze first to ethionic acid and then to isethionic acid. The hydrolysis of ethionic acid to produce isethionic acid and sulfuric acid has also been described in Wooten and Lloyd, J. Org. Chem. 39, 2112 (1974) and Weinreich and Jufreso, Bull. Soc. Chem. France 1965 (3) 787; which indicate that the hydrolysis readily occurs under aqueous acid conditions. These processes all have in common the requirement of the use of sulfur trioxide, a violent reagent requiring careful and special handling techniques, and the intermediacy of carbyl sulfate or ethionic acid, which must then be hydrolyzed in aqueous solution to isethionic acid resulting in the production of sulfuric acid as a by-product. Due to the use of water as a solvent the resulting isethionic acid is obtained in a dilute solution and of concentrated is obtained as the monohydrate. Generally, these processes are not used to obtain isethionic acid per se but rather the hydrolysis mixture is neutralized with alkaline earth bases such as calcium or barium salts to precipitate the insoluble sulfate followed by the addition of alkali thereby forming the isethionate salt.

U.S. Pat. No. 4,499,028 discloses a process for the preparation of isethionic acid by treating alkali metal isethionate with hydrochloric acid in aqueous medium. This process requires excess hydrochloric acid which is not easily recovered for reuse. This process results in yields of about 80% isethionic acid containing alkali metal isethionates and water.

None of the methods of preparing isethionic acid disclosed in the prior art yield isethionic acid substantially free of contaminants such as chloride ion, sodium ion, sulfuric acid and water nor are they economical.

It is therefore an object of the present invention to provide a novel process for the preparation of isethionic acid.

It is a further object of the invention to provide a process for the preparation of isethionic acid which avoids undesirable contaminants.

It is a still further object of the invention to provide an economically desirable process for the preparation of isethionic acid.

These and other objects of the present invention will become apparent to one skilled in the art from the detailed description given hereinafter.

SUMMARY OF THE INVENTION

This invention relates to a process for the preparation of isethionic acid involving the reaction of sodium isethionate and hydrogen chloride in an alcoholic solvent.

DETAILED DESCRIPTION OF THE INVENTION

The present invention relates to a process comprising reacting sodium isethionate with hydrogen chloride in the presence of a suitable alcohol resulting in the formation of isethionic acid.

This reaction should be carried out in an alcoholic solvent system wherein the alcohol is a straight or branched chain lower alkanol containing from 1 to 4 carbon atoms. A preferred alcohol solvent is ethanol.

In the process of the present invention it is important that anhydrous sodium isethionate and anhydrous hydrogen chloride are utilized to prevent contamination and insure the purity and yield of the desired product.

The reaction is preferably carried out at room temperature but may be carried out at elevated temperatures up to the boiling point of the solvent, if the rate of reaction requires. After completion, the resultant product is filtered to remove the insoluble solids, and then the alcohol and axcess hydrogen chloride is distilled off yielding substantially pure isethionic acid. The yields approach 100% bases on the sodium isethionate provided that equimolar amounts of sodium isethionate and hydrogen chloride or an excess of hydrogen chloride is utilized.

Isethionic acid is useful in electroplating; in the manufacture of inks; in the preparation of resins; as a reaction catalyst, for example, isethionic acid serves as a catalyst in the condensation reaction of aniline with formaldehyde to prepare diaminodiphenylmethanes; and as a reagent in the preparation of surfactants which are useful in the formulation of personal care and cleaning products.

Specific embodiments of the present invention are illustrated by the following representative examples. It will be understood, however, that the invention is not confined to the specific limitations set forth in the individual examples, but rather to the scope of the appended claims.

EXAMPLE I

In a suitable reaction apparatus equipped with condenser, stirrer and cooling means and protected from atmospheric moisture, are combined 78 g of dry sodium isethionte and 100 ml anhydrous ethanol. Excess dry hydrogen chloride gas is introduced by a suitable dispersion means into the stirred mixture with cooling for about ½ hour, such that the temperature does not exceed 60° C. After removal of precipitated sodium chloride by filtration, the alcohol and excess hydrogen chloride are distilled off under vacuum. The residue of 123 g of liquid isethionic acid solidifies on cooling. It has an equivalent weight (sodium hydroxide titration) of 135, and is free of chloride ion.

EXAMPLE II

In a suitable reactor equipped with condenser, stirrer and cooling means protected from atmospheric moisture is placed 505 g of ethanol. Dry hydrogen chloride gas is introduced by a suitable dispersion means until 154 g (3.44 mole) is absorbed.

To the above solution is added with stirring 503 g (3.4 moles) of sodium isethionate in portions over 1 hour. The mixture is stirred for an additional 30 min. It is then filtered and the solvent removed by distillation to produced 435 g of isethionic acid (quantitative yield, equivalent weight 126, with negligible chloride content).

EXAMPLE III

In a suitable reactor is placed 2-propanol (500 g) and HCl gas is introduced with cooling until 141 g (3.91 moles) is absorbed.

Sodium isethionate (193 g, 1.3 moles) is added, and the mixture stirred at room temperature for 16 hours. After filtration and evaporation of HCl/alcohol 164 g of isethionic acid (quantitative yield) is obtained.

EXAMPLE IV

In a suitable reactor are combined 1000 ml of isopropanol solution of hydrogen chloride (HCl content 111 g, 3.08 moles) and sodium isethionate (228 g, 1.54 moles). The mixture is heated at the boil for two hours. After cooling, filtration and evaporation, 194 g of isethionic acid (quantitative yield) is recovered.

EXAMPLE V

In a suitable reaction apparatus equipped with stirring, vacuum and heating utilities, and equipped with distillation condenser are combined lauric acid (200 parts) and isethionic acid (150 parts, 20% excess). The reaction mixture is heated under <1 mmHg pressure to 125° C. over 2 hours, to produce lauroyl isethionic acid of 87% activity. After cooling to 75° C., the reaction mass is transferred to a solution of 175 parts of triethanolamine in 1000 parts of water. The mixture is vigorously stirred at 45° C. to produce a homogeneous solution at pH 6.2 of the triethanolamine salt of lauroyl isethionic acid of 24.4% activity (96% conversion) which is useful as a surfactant.

In addition to the preferred embodiments described herein, other embodiments, arrangements and variations within the scope of the invention and the scope of the appended claims will be apparent to those skilled in the art.

What is claimed is:

1. A process for the preparation of isethionic acid under anhydrous conditions comprising contacting anhydrous sodium isethionate with anhydrous hydrogen chloride in the presence of an alcohol solvent.

2. The process of claim 1 wherein the solvent is a lower alkanol containing from 1 to 4 carbon atoms.

3. The process of claim 2 wherein the solvent is ethanol.

* * * * *